United States Patent
Modi (10) Patent No.: US 7,087,215 B2
(45) Date of Patent: *Aug. 8, 2006

(54) METHODS OF ADMINISTERING AND ENHANCING ABSORPTION OF PHARMACEUTICAL AGENTS

(75) Inventor: Pankaj Modi, Ancaster (CA)

(73) Assignee: Generex Pharmaceuticals Incorporated, Toronto (CA)

( * ) Notice: Subject to any disclaimer, the term of this patent is extended or adjusted under 35 U.S.C. 154(b) by 137 days.

This patent is subject to a terminal disclaimer.

(21) Appl. No.: 10/222,240

(22) Filed: Aug. 16, 2002

(65) Prior Publication Data

US 2003/0157029 A1 Aug. 21, 2003

Related U.S. Application Data

(63) Continuation-in-part of application No. 09/574,504, filed on May 19, 2000, now Pat. No. 6,451,286, which is a continuation-in-part of application No. 09/519,285, filed on Mar. 6, 2000, now Pat. No. 6,375,975, which is a continuation-in-part of application No. 09/386,284, filed on Aug. 31, 1999, now Pat. No. 6,312,665, which is a continuation-in-part of application No. 09/251,464, filed on Feb. 17, 1999, now Pat. No. 6,436,367.

(60) Provisional application No. 60/113,239, filed on Dec. 21, 1998.

(51) Int. Cl.
*A61K 9/12* (2006.01)
*A61K 9/127* (2006.01)
*A61K 9/107* (2006.01)

(52) U.S. Cl. .......................... 424/45; 424/46; 424/434; 424/455; 424/464; 514/2; 514/3; 514/866; 514/946

(58) Field of Classification Search ................ 424/45, 424/489, 46, 434, 43, 455, 464; 514/2, 3, 514/282, 866, 946

See application file for complete search history.

(56) References Cited

U.S. PATENT DOCUMENTS

| | | |
|---|---|---|
| 4,156,719 A | 5/1979 | Sezaki et al. |
| 4,582,835 A | 4/1986 | Lewis et al. |
| 4,614,730 A | 9/1986 | Hansen et al. |
| 4,661,492 A | 4/1987 | Lewis et al. |
| 4,673,679 A | 6/1987 | Aungst et al. |
| 4,900,730 A | 2/1990 | Miyauchi |
| 5,004,611 A | 4/1991 | Leigh |
| 5,053,389 A | 10/1991 | Balschmidt et al. |
| 5,230,884 A | 7/1993 | Evans et al. |
| 5,240,932 A | 8/1993 | Morimoto et al. |
| 5,292,499 A | 3/1994 | Evans et al. |
| 5,306,483 A | 4/1994 | Mautone |
| 5,376,646 A | 12/1994 | Pittrof et al. |
| 5,451,408 A | 9/1995 | Mezei et al. |
| 5,492,688 A | 2/1996 | Byron et al. |
| 5,514,670 A | 5/1996 | Friedman et al. |
| 5,569,450 A | 10/1996 | Duan et al. |
| 5,591,713 A | 1/1997 | Igari et al. |
| 5,629,011 A | 5/1997 | Illum |
| 5,653,987 A | 8/1997 | Modi et al. |
| 5,656,277 A | 8/1997 | Berlati et al. |
| 5,665,700 A | 9/1997 | Cho et al. |
| 5,690,954 A | 11/1997 | Illum |
| 5,747,066 A | 5/1998 | Pittrof et al. |
| 5,747,445 A | 5/1998 | Backstrom et al. |
| 5,981,591 A | 11/1999 | Deihl |
| 6,017,545 A | 1/2000 | Modi |
| 6,042,811 A | 3/2000 | Duan et al. |
| 6,090,407 A | 7/2000 | Knight et al. |
| 6,110,486 A | 8/2000 | Dugger, III |
| 6,193,997 B1 | 2/2001 | Modi |
| 6,214,375 B1 | 4/2001 | Modi |
| 6,221,378 B1 | 4/2001 | Modi |
| 6,225,343 B1 | 5/2001 | Behl et al. |
| 6,255,502 B1 | 7/2001 | Penkler et al. |
| 6,261,539 B1 | 7/2001 | Adjei et al. |
| 6,271,200 B1 | 8/2001 | Modi |
| 6,294,153 B1 | 9/2001 | Modi |
| 6,312,665 B1 | 11/2001 | Modi |
| 6,375,975 B1 | 4/2002 | Modi |
| 6,432,383 B1 * | 8/2002 | Modi ........................ 424/43 |
| 6,436,367 B1 | 8/2002 | Modi |
| 6,451,286 B1 | 9/2002 | Modi |
| 6,485,706 B1 * | 11/2002 | McCoy et al. ................ 424/45 |

(Continued)

FOREIGN PATENT DOCUMENTS

EP 0 200 383 12/1986

(Continued)

OTHER PUBLICATIONS

Worsley et al, Inhaled Fentanyl as a method of analgesia, 1990, The Association of Anesthetists of Gt Britain and Ireland, vol. 45, pp. 449-451.*

(Continued)

*Primary Examiner*—Sreenivasin Padmanabhan
*Assistant Examiner*—Mina Haghighatian
(74) *Attorney, Agent, or Firm*—Hamilton, Brook, Smith & Reynolds, P.C.

(57) ABSTRACT

Pharmaceutical compositions comprising a macromolecular pharmaceutical agent in mixed micellar form are disclosed. The mixed micelles are formed from an alkali metal alkyl sulfate, and at least three different micelle-forming compounds as described in the specification. Micelle size ranges between about 1 and 10 nanometers. Methods for administering the compositions are also disclosed. A preferred method for administering the present composition is through the buccal region of the mouth, which has been demonstrated to achieve peak plasma levels of the pharmaceutical agent in about thirty minutes.

16 Claims, 3 Drawing Sheets

U.S. PATENT DOCUMENTS

| | | |
|---|---|---|
| 6,495,120 B1 | 12/2002 | McCoy et al. |
| 6,524,557 B1 * | 2/2003 | Backstrom et al. ............ 424/46 |
| 2003/0017119 A1 * | 1/2003 | Rabinowitz et al. .......... 424/46 |

FOREIGN PATENT DOCUMENTS

| | | |
|---|---|---|
| EP | 0 272 097 | 6/1988 |
| WO | WO 96/36352 | 11/1996 |
| WO | WO 96/40057 | 12/1996 |
| WO | WO 97/42938 | 11/1997 |
| WO | WO 99/22703 | 5/1999 |
| WO | WO 99/40932 | 8/1999 |
| WO | WO 00/18371 | 4/2000 |
| WO | WO 0/037051 | 6/2000 |
| WO | WO 00/47203 | 8/2000 |
| WO | WO 00/56291 | 9/2000 |
| WO | WO 01/17506 | 3/2001 |
| WO | WO 01/87268 A1 | 11/2001 |

OTHER PUBLICATIONS

Editor Alfonso R. Gennaro, Remington's Pharmaceutical Sciences, 17 Edition, 1985, pp. 293-297 & 1662-1677, Mack Publishing Company, Easton, Pennsylvania 18042.

Dieter Kohler, Systemic Therapy with Aerosols, Aerosols in Medicine: Principles, Diagnosis and Therapy, 2nd rev. ed., pp. 303-319, 1993 Elsevier Science Publishers BV.

Vincent HL Lee et al., Mucosal Penetration Enhancers for Facilitation of Peptide and Protein Drug Absorption, Critical Reviews in Therapeutic Drug Carrier Systems, pp. 91.139.140. 8(2):91-192 (1991).

John S. Patton. et al., Pulmonary Delivery of Peptides and Proteins, Advanced Drug Delivery Reviews, pp. 179-196, 8 (1992), Elsevier Science Publishers BV.

Hans Schreier et al., Pulmonary Delivery of Liposomes, Journal of Controlled Release, pp. 209-223, 24 (1993) Elsevier Science Publishers BV.

Amir H. Shojaei, Buccal Mucosa as a Route for Systemic Drug Delivery: A Review, J Pharm Pharmaceut Sci, 1 (1):1:15-30, 1998.

CK Oh et al., Biopharmaceutic Aspects of Buccal Absorption of Insulin, Meth Find Exp Clin Pharmacol 1990: 12(3):205-212.

Bruce J. Aungst, Comparison of the Effects of Various Transmucosal Absorption Promoters on Buccal Insulin Delivery, International Journal of Pharmaceutics, 53 (1989) 227-235.

Bruce J. Aungst et al., Comparison of Nasal, Rectal, Buccal, Sublingual and Intramuscular Insulin Efficiency and the Effects of a Bile Salt Absorption Promoter, The Journal of Pharmacology and Experimental Therapeutics, vol. 244, No. 1, pp. 23-27, 1988.

Bruce J. Aungst et al., Site Dependence of Absorption-Promoting Actions of Laureth-9, Na Salicylate, Na2EDTA and Aprotinin on Rectal, Nasal and Buccal Insulin Delivery, Pharmaceutical Research, vol. 5, No. 5, 1988. pp. 305-308.

Parkpoom Pengamnuay et al., Bile Salt-Fatty Acid Mixed Micelles as Nasal Absorption Promoters of Peptides, II. In Vivo Nasal Absorption of Insulin in Rats and Effects of Mixed Micelles on the Morphological Integrity of the Nasal Mucosa, Pharmaceutical Research, vol. 7, No. 4, 1990, pp. 370-375.

* cited by examiner

METHODS OF ADMINISTERING AND ENHANCING ABSORPTION OF PHARMACEUTICAL AGENTS

CROSS REFERENCE TO RELATED APPLICATIONS

This application is a continuation-in-part of U.S. application Ser. No. 09/574,504, filed May 19, 2000, now U.S. Pat. No. 6,451,286 which is a continuation-in-part of U.S. application Ser. No. 09/519,285, filed Mar. 6, 2000, now U.S. Pat. No. 6,375,975 which is a continuation-in-part of U.S. application Ser. No. 09/386,284 filed Aug. 31, 1999, now U.S. Pat. No. 6,312,665 which is a continuation-in-part of U.S. application Ser. No. 09/251,464 filed Feb. 17, 1999, now U.S. Pat. No. 6,436,367 which claims priority to provisional Application No. 60/113,239 filed Dec. 21, 1998.

FIELD OF THE INVENTION

The present invention relates to an improved pharmaceutical composition comprising macromolecule pharmaceuticals in micellar form. The pharmaceutical compositions are particularly effective in buccal and pulmonary applications. The present invention further relates to methods for preparing and using these pharmaceutical compositions. Methods for enhancing the rate of absorption of a macromolecular pharmaceutical agent are also disclosed. Peak plasma levels of the pharmaceutical agent can be obtained in about thirty minutes.

BACKGROUND INFORMATION

Relatively little progress has been made over the years in reaching the target of safe and effective oral formulations for macromolecules, including peptides and proteins. Barriers to developing oral formulations for proteins and peptides include poor intrinsic permeability, lumenal and cellular enzymatic degradation, rapid clearance, and chemical instability in the gastrointestinal (GI) tract. Pharmaceutical approaches to address these barriers that have been successful with traditional small, organic drug molecules have not readily translated into effective peptide and protein formulations.

Various routes of administration other than injection for proteins and peptides have been explored with little or no success. Oral and nasal cavities have been of particular interest. The ability of molecules to permeate the oral mucosae appears to be related to molecular size, lipid solubility and peptide protein ionization. Molecules less than 1000 daltons appear to cross oral mucosae rapidly. As molecular size increases, the permeability of the molecule decreases rapidly. Lipid soluble compounds are more permeable than non-lipid soluble molecules. Maximum absorption occurs when molecules are un-ionized or neutral in electrical charges. Charged molecules, therefore, present the biggest challenges to absorption through the oral mucosae.

Most proteinic drug molecules are extremely large molecules with molecular weights exceeding 6000 daltons. In addition to being large, these molecules typically have very poor lipid solubility, and are often practically impermeable. Substances that facilitate the absorption or transport of large molecules (i.e., >1000 daltons) across biological membranes are referred to in the art as "enhancers" or "absorption aids". These compounds generally include chelators, bile salts, fatty acids, synthetic hydrophilic and hydrophobic compounds, and biodegradable polymeric compounds. Many enhancers lack a satisfactory safety profile respecting irritation, lowering of the barrier function, and impairment of the mucocilliary clearance protective mechanism.

Some enhancers, especially those related to bile salts, and some protein solubilizing agents give an extremely bitter and unpleasant taste. This makes their use almost impossible for human consumption on a daily basis. Several approaches attempting to address the taste problem relating to the bile salt-based delivery systems include patches for buccal mucosa, bilayer tablets, controlled release tablets, use of protease inhibitors, and various polymer matrices. These technologies fail to deliver proteinic drugs in the required therapeutic concentrations, however. Further, the film patch devices result in severe tissue damage in the mouth. Other attempts to deliver large molecules via the oral, nasal, rectal, and vaginal routes using single bile acids or enhancing agents in combination with protease inhibitors and biodegradable polymeric materials similarly failed to achieve therapeutic levels of proteinic drugs in the patient. Single enhancing agents fail to loosen tight cellular junctions in the oral, nasal, rectal and vaginal cavities for the time needed to permit passage of large molecules through the mucosal membranes without further degradation. These problems make it impractical to use many systems. Accordingly, there remains a need for improved therapeutic formulations, particularly those comprising macromolecules and particularly those useful for buccal and pulmonary application. Methods for manufacture and use of such formulations are also needed.

SUMMARY OF THE INVENTION

The present invention addresses the above need by providing an improved pharmaceutical composition comprising a macromolecular pharmaceutical agent, an alkali metal alkyl sulfate, and at least three additional micelle-forming compounds, in a suitable solvent. The agent can be one or more proteins, peptides, hormones, vaccines or drugs. The molecular weight of the macromolecular pharmaceutical agent preferably ranges between about 1,000 and 2,000,000 daltons. The agent is presented in mixed micellar form, with a micelle size of approximately one to 10 nanometers (nm).

As used herein the term "mixed micelles" refers to at least two different types of micelles each of which has been formed using different micelle forming compounds; for example, the present compositions comprise a mix of at least four different types of micelles—micelles formed between the pharmaceutical agent and alkali metal alkyl sulfate, and micelles formed between the pharmaceutical agent and at least three different additional micelle forming compounds as disclosed herein. It will be understood that each individual micelle can be formed from more than one micelle-forming compound as well. The mixed micelles of the present invention tend to be smaller than the pores of the membranes in the oral cavity or the GI tract. It is therefore believed that the extremely small size of the present mixed micelles helps the encapsulated macromolecules penetrate efficiently through the oral mucosae. Thus, the present compositions offer increased bioavailability of active drug, particularly across oral mucosae, when compared with pharmaceutical preparations known in the art.

The present invention is also directed to a method for enhancing the rate of absorption of a macromolecular pharmaceutical agent comprising administering a composition comprising the agent in combination with an alkali metal alkyl sulfate and at least three micelle-forming compounds. Such a method is particularly effective when the composition is administered to the buccal region. Peak plasma levels of the pharmaceutical agent can be obtained within about 30 minutes or less, using the methods of administration of the present invention.

Methods for making and using the present pharmaceutical compositions are also within the scope of the present invention.

It is therefore an aspect of the present invention to provide a pharmaceutical composition comprising a macromolecular pharmaceutical agent and a combination of micelle forming compounds.

It is a further aspect of the invention to provide such a composition wherein the macromolecular pharmaceutical agent is in micellar form.

It is a further aspect of the invention to provide a method for administering macromolecular pharmaceutical agents, particularly to the buccal and pulmonary regions of a patient.

A further aspect of the invention is to provide methods for making pharmaceutical compositions comprising macromolecular pharmaceutical agents and micelle forming compounds.

It is an additional aspect of the invention to provide peak plasma levels of the pharmaceutical agent within a very short period of time, e.g., within about 30 minutes of administration.

These and other aspects of the invention will be apparent from the following disclosure and appended claims.

BRIEF DESCRIPTION OF THE DRAWINGS

The invention is further illustrated by the following non-limited drawings in which.

DETAILED DESCRIPTION OF THE INVENTION

The present invention is directed to a pharmaceutical composition comprising: an effective amount of a macromolecular pharmaceutical agent; an alkali metal alkyl sulfate; at least three micelle-forming compounds selected from the group consisting of lecithin, hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogues thereof and mixtures or combinations thereof; and a suitable solvent. The alkali metal alkyl sulfate concentration is between about 0.1 and 20 wt./wt. % of the total composition, each micelle-forming compound concentration is between about 0.1 and 20 wt./wt. % of the total composition, and the total concentration of the alkali metal alkyl sulfate and the micelle-forming compounds together is less than 50 wt./wt. % of the composition.

As used herein, the term "macromolecular" refers to pharmaceutical agents having a molecular weight greater than about 1000 daltons; preferably the macromolecular pharmaceutical agents of the present invention have a molecular weight between about 2000 and 2,000,000 daltons, although even larger molecules are also contemplated.

The term "pharmaceutical agent" as used herein covers a wide spectrum of agents, and can include agents used for both human and veterinary applications including but not limited to treatment and study. The term broadly includes proteins, peptides, hormones, vaccines and drugs.

Preferred pharmaceutical agents include insulin, heparin, low molecular weight heparin (molecular weight less than about 5000 daltons), hirulog, hirugen, huridine, interferons, cytokines, mono and polyclonal antibodies, immunoglobins, chemotherapeutic agents, vaccines, glycoproteins, bacterial toxoids, hormones, calcitonins, glucagon like peptides (GLP-1), large molecular antibiotics (i.e., greater than about 1000 daltons), protein based thrombolytic compounds, platelet inhibitors, DNA, RNA, gene therapeutics, antisense oligonucleotides, opioids, narcotics, hypnotics, steroids and pain killers.

Hormones which may be included in the present compositions include but are not limited to thyroids, androgens, estrogens, prostaglandins, somatotropins, gonadotropins, erythropoetin, interferons, steroids and cytokines. Cytokines are small proteins with the properties of locally acting hormones and include, but are not limited to, various forms of interleukin (IL) and growth factors including various forms of transforming growth factor (TGP), fibroblast growth factor (FGF) and insulin-like growth factor (IGF). Vaccines which may be used in the compositions according to the present invention include bacterial and viral vaccines such as vaccines for hepatitis, influenza, tuberculosis, canary pox, chicken pox, measles, mumps, rubella, pneumonia, BCG, HIV and AIDS; bacterial toxoids include but are not limited to diphtheria, tetanus, *Pseudomonas* sp. and *Mycobacterium tuberculosis*. Examples of drugs, more specifically cardiovascular or thrombolytic agents, include heparin, hirugen, hirulos and hirudine. Macromolecular pharmaceutical agents included in the present invention further include monoclonal antibodies, polyclonal antibodies and immunoglobins. This list is not intended to be exhaustive.

A preferred macromolecular pharmaceutical agent according to the present invention is insulin. "Insulin" as used herein encompasses naturally extracted human insulin, or competently produced human insulin, insulin extracted from bovine, porcine or other mammalian sources, recombinantly produced human, bovine, porcine or other mammalian insulin, insulin analogues, insulin derivatives, and mixtures of any of these insulin products. The term further encompasses the insulin polypeptide in either its substantially purified form, or in its commercially available form in which additional excipients are added. Various forms of insulin are widely commercially available. An "insulin analogue" encompasses any of the insulins defined above wherein one or more of the amino acids within the polypeptide chain has been replaced with an alternative amino acid, wherein one or more of the amino acids have been deleted, or wherein one or more amino acids is added. "Derivatives" of insulin refers to insulin or analogues thereof wherein at least one organic substituent is bound to one or more of the amino acids in the insulin chain.

The macromolecular pharmaceutical agent exists in micellar form in the present pharmaceutical compositions. As will be appreciated by those skilled in the art, a micelle is a colloidal aggregate of amphipathic molecules in which the polar hydrophilic portions of the molecule extend outwardly while the non-polar hydrophobic portions extend inwardly. As discussed below, various combinations of micelle-forming compounds are utilized in order to achieve the present formulation. It is believed that the presence of the micelles significantly aids in the absorption of the macromolecular pharmaceutical agent both because of their enhanced absorption ability, and also because of their size. In addition, encapsulating pharmaceutical agents in micelles protects the agents from rapid degradation in the GI environment.

The particle size of the micelles will typically be in the range of 1 to 10 nanometers, many will range between 1 and 5 nanometers in size. The shape of the micelle can vary and can be, for example, prolate, oblate or spherical; spherical micelles are most typical.

An effective amount of the macromolecular pharmaceutical agent should be included in the present composition. As used herein, the term "effective amount" refers to that amount of the pharmaceutical agent needed to bring about the desired result, such as obtaining the intended treatment or prevention of a disorder in a patient, or regulating a physiological condition in a patient. Such an amount will therefore be understood as having a therapeutic and/or prophylactic effect in a patient. As used herein, the term "patient" refers to members of the animal kingdom, including but not limited to humans. It will be appreciated that the effective amount will vary depending on the particular agent used, the parameters determined for the agent, the nature and severity of the disorder being treated, the patient being treated, and the route of administration. The determination of what constitutes an effective amount is well within the skill of one practicing in the art. Typically, the present formulations will contain pharmaceutical agents in a concentration between about 0.1 and 20 wt./wt. % of the total composition, more preferably between about 1 and 10 wt./wt.

Any alkali metal alkyl sulfate can be used in the present compositions, provided compatibility problems do not arise. Preferably, the alkyl is a C8 to C22 alkyl, more preferably lauryl (C12). Any alkali metal can be utilized, with sodium being preferred. The alkali metal alkyl sulfate is generally present in a concentration of between about 0.1 and 20 wt./wt. % of the total composition; a concentration of less than about 5 wt./wt. % of the total composition is preferred.

The compositions of the present invention further comprise at least three micelle-forming compounds selected from the group comprising lecithin, hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxocholanyl glycine, glycerin, polyglycerin, lysine, polylysine, triolein, polyoxyethylene ethers, polidocanol alkyl ethers, chenodeoxycholate and deoxycholate. Pharmaceutically acceptable salts and analogues of any of these compounds are also within the present scope as are mixtures or combinations of any of these compounds. Each of the three, or more, micelle-forming compounds listed above is present in the compositions in a concentration of between about 0.1 and 20 wt./wt. % of the total composition. More preferably, each of these micelle-forming compounds is present in a concentration of less than about 5 wt./wt. % of the total composition. For delivery of the present macromolecular pharmaceutical agents, particularly insulin, use of three or more micelle-forming compounds achieves a cumulative effect in which the amount of pharmaceutical agent that can be delivered is greatly increased as compared to when only one or two micelle-forming compounds are used. Use of three or more micelle-forming compounds also enhances the stability of the pharmaceutical agent compositions.

The alkali metal alkyl sulfate functions as a micelle forming agent, and is added to the composition in addition to the three or more other micelle-forming compounds listed herein. The total concentration of alkali metal alkyl sulfate and the three or more additional micelle-forming compounds together is less than 50 wt./wt. % of the composition.

It will be appreciated that several of the micelle-forming compounds are generally described as fatty acids, bile acids, or salts thereof. The best micelle-forming compounds to use may vary depending on the pharmaceutical agent used and can be readily determined by one skilled in the art. In general, bile salts are especially suitable for use with hydrophilic drugs and fatty acid salts are especially suitable for use with lipophilic drugs. Because the present invention uses relatively low concentrations of bile salts, problems of toxicity associated with the use of these salts is minimized, if not avoided.

The lecithin can be saturated or unsaturated, and is preferably selected from the group consisting of phosphatidylcholine, phosphatidylserine, sphingomyelin, phosphatidylethanolamine, cephalin, and lysolecithin.

Preferred salts of hyaluronic acid are alkali metal hyaluronates, especially sodium hyaluronate, alkaline earth hyaluronates, and aluminum hyaluronate. When using hyaluronic acid or pharmaceutically acceptable salts thereof in the present compositions, a concentration of between about 0.1 and 5 wt./wt. % of the total composition is preferred, more preferably less than about 3.5 wt./wt. %.

Particularly suitable micelle-forming compound combinations include i) sodium hyaluronate, monoolein and saturated phospholipid, ii) saturated phospholipid, monoolein and glycolic acid, iii) sodium hyaluronate, polyoxyethylene ether and lecithin, iv) polyoxyethylene ether, trihydroxy oxocholanyl glycine and lecithin, v) polidocanol 9 lauryl ether, polylysine and triolein, vi) saturated phospholipid, polyoxyethylene ether and glycolic acid, vii) trihydroxy oxocholanyl glycine, lecithin and chenodeoxycholate; viii) trihydroxy oxocholanyl glycine, deoxycholate and glycerin; ix) polidocanol 10 lauryl ether, sodium oxocholanyl glycine and lecithin; x) polidocanol 10 lauryl ether, phosphatidyl choline and oleic acid; xi) polidocanol 10 lauryl ether, sodium hyaluronate and lecithin; and xii) polidocanol 20 lauryl ether, evening of primrose oil and lecithin.

The above-described components of the present composition are contained in a suitable solvent. The term "suitable solvent" is used herein to refer to any solvent in which the components of the present invention can be solubilized, in which compatibility problems do not arise, and which can be administered to a patient. Any suitable aqueous or nonaqueous solvent can be used. A particular preferred solvent is water. Other suitable solvents include alcohol solutions, especially ethanol. Alcohol should be used at concentrations that will avoid precipitation of the components of the present compositions. Enough of the solvent should be added so that the total of all of the components in the composition is 100 wt./wt. %, i.e., solvent to q.s. Typically, some portion of the solvent will be used initially to solubilize the pharmaceutical agent prior to the addition of the micelle-forming compounds.

The present compositions optionally contain a stabilizer and/or a preservative. Phenolic compounds are particularly suited for this purpose as they not only stabilize the composition, but they also protect against bacterial growth and help absorption of the composition. A phenolic compound will be understood as referring to a compound having one or more hydroxy groups attached directly to a benzene ring. Preferred phenolic compounds according to the present invention include phenol and methyl phenol (also known as m-cresol), and mixtures thereof.

The compositions of the present invention can further comprise one or more of the following: inorganic salts; antioxidants; protease inhibitors; and isotonic agents. The amount of any of these optional ingredients to use in the present compositions can be determined by one skilled in the art. It will be understood by those skilled in the art that colorants, flavoring agents and non-therapeutic amounts of other compounds may also be included in the formulation. Typical flavoring agents are menthol, sorbitol and fruit flavours. When menthol is used as one of the micelle-forming compounds, therefore, it will also impart flavor to the composition.

For example, some compositions, including those which contain insulin, may also contain at least one inorganic salt; the salt should be one which opens channels in the GI tract and which may provide additional stimulation to release insulin. Non-limiting examples of inorganic salts are sodium, potassium, calcium and zinc salts, especially sodium chloride, potassium chloride, calcium chloride, zinc chloride and sodium bicarbonate.

It will be recognized by those skilled in the art that for many pharmaceutical compositions it is usual to add at least one antioxidant to prevent degradation and oxidation of the pharmaceutically active ingredients. The antioxidant can be selected from the group consisting of tocopherol, deteroxime mesylate, methyl paraben, ethyl paraben, ascorbic acid and mixtures thereof, as well as other antioxidants known in the pharmaceutical arts. A preferred antioxidant is tocopherol. The parabens will also provide preservation to the composition.

Protease inhibitors serve to inhibit degradation of the pharmaceutical agent by the action of proteolytic enzymes. When used, protease inhibitors are preferably in a concentration of between about 0.1 and 3 wt./wt. % of the composition. Any material that can inhibit proteolytic activity can be used, absent compatibility problems. Examples include but are not limited to bacitracin and bacitracin derivatives such as bacitracin methylene disalicylates, soybean trypsin, and aprotinin. Bacitracin and its derivatives are preferably used in a concentration of between 1.5 and 2 wt./wt. % of the total composition, while soyabean trypsin and aprotinin are preferably used in a concentration of between about 1 and 2 wt./wt. % of the total composition.

An isotonic agent such as glycerin or dibasic sodium phosphate may also be added after formation of the mixed micellar composition. The isotonic agent serves to keep the micelles in solution. When glycerin is used as one of the micelle-forming compounds it will also function as an isotonic agent. When dibasic sodium phosphate is used it will also serve to inhibit bacterial growth.

The pH of the present pharmaceutical composition should typically be in the range of 5 to 8, more preferably 6 to 7. Hydrochloric acid or sodium hydroxide can be utilized to adjust the pH of the composition as needed.

The compositions of the present invention may be stored at room temperature or at cold temperature. Storage of proteinic drugs is preferable at a cold temperature to prevent degradation of the drugs and to extend their shelf life.

The present invention, therefore, provides a pharmaceutical composition in which a macromolecular pharmaceutical agent is encapsulated in mixed micelles formed by a combination of micelle-forming agents. The composition can be delivered through buccal or pulmonary means, with buccal being preferred. Both the oral and nasal membranes offer delivery advantages, in that drugs administered through these membranes have a rapid drug absorption and a rapid onset of action, provide therapeutic plasma levels, avoid the first pass effect of hepatic metabolism, and avoid exposure of the drug to the hostile GI environment. An additional advantage is the easy access to membrane sites, so that the drug can be applied, localized and removed easily.

Oral routes of administration may be particularly advantageous. The sublingual mucosa includes the membrane of the ventral surface of the tongue and the floor of the mouth, and the buccal mucosa is the lining of the cheeks. The sublingual and buccal mucosae are relatively permeable, allowing for the rapid absorption and acceptable bioavailability of many drugs. Further, the buccal and sublingual mucosae are convenient, non-evasive and easily accessible. In comparison to the GI tract and other organs, the buccal environment has lower enzymatic activity and a neutral pH that allows for a longer effective life of the drug in vivo. The sublingual mucosa and buccal mucosa are collectively referred to herein as the "oral mucosae".

It is believed that improvements in penetration and absorption of the present mixed micellar formulations can be achieved by administering the present compositions with propellants such as tetrafluoroethane, heptafluoroethane, dimethylfluoropropane, tetrafluoropropane, butane, isobutane, dimethyl ether and other non-CFC and CFC propellants. Preferably, the ratio of pharmaceutical agent to propellant is from 5:95 to 25:75. The preferred propellants are hydrogen-containing chlorofluorocarbons, hydrogen-containing fluorocarbons, dimethyl ether and diethyl ether. Even more preferred is HFA-134a (1,1,1,2-tetrafluoroethane).

Preferably, the present compositions are delivered through metered dose inhalers or spray devices. Metered dose inhalers are known and are a popular pulmonary drug delivery form for some drugs. One benefit of using a metered dose device is the ability to deliver a precise amount of medication with each application, and another is that the potential for contamination is minimized because the devices are self-contained.

The present invention also provides a process for making the pharmaceutical composition of the present invention. The present compositions may be prepared by mixing a solution of the macromolecular pharmaceutical agent, the alkali metal alkyl sulfate, at least three micelle-forming compounds, and optionally the stabilizer and other additives. The pharmaceutical agent should be added in an amount effective for the desired purpose. The micelle-forming compounds may be added concurrently or sequentially. Mixed micelles will form with substantially any kind of mixing of the ingredients but vigorous mixing is preferred in order to provide micelles of about 10 nanometers or less in size. The pharmaceutical agents, solvents, alkali metal alkyl sulfates, micelle-forming compounds and optional additives as described above for the present compositions are all suitable for use in the present processes.

In one method a first micellar composition is prepared by mixing a solution comprising the pharmaceutically active agent with at least the alkali metal alkyl sulfate to form the first micellar composition. The first micellar composition is then mixed with at least three additional micelle-forming compounds to form a mixed micellar composition. In another method, a first micellar composition is prepared by mixing a solution containing the pharmaceutically active agent, the alkali metal alkyl sulfate and at least one additional micelle-forming compound; to the composition is then added the remaining micelle-forming compounds, with vigorous mixing. The alkali metal alkyl sulfate and three or more micelle-forming compounds should not be added to the pharmaceutical agent solution all at once.

The stabilizer, preferably phenol and/or m-cresol, may be added to the mixed micellar composition to stabilize the formulation and protect against bacterial growth. Alternatively, the stabilizer may be added at the same time as any of the micelle-forming ingredients. An isotonic agent may also be added after formation of the mixed micellar composition. Similarly, any of the other optional additives as described above can be added at this time. The formulation can then be put into an aerosol dispenser and the dispenser charged with propellant, if administration by this route is desired. The propellant, which is under pressure, is in liquid form in the dispenser. When the composition of the present invention is in a dispenser, the aqueous phase may be separated from the propellant phase. Preferably, however, the ratios of the ingredients are adjusted by simple experimentation so that the aqueous and propellant phases become one, i.e., there is one phase. If there are two phases, it may be necessary to shake the dispenser prior to dispensing a portion of the contents, such as through a metered valve. The dispensed dose of pharmaceutical agent is propelled from the metered valve in a fine spray.

One specific embodiment of the present processes provides for making the present pharmaceutical compositions by:

a) mixing a macromolecular pharmaceutical agent in a suitable solvent with an alkali metal alkyl sulfate, and adding to the mixture at least three micelle-forming compounds selected from the group consisting of lecithin, hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine, glycerin, polyglycerin, lysine, polylysine, triolein, polyoxyethylene ethers, polidocanol alkyl ethers, chenodeoxycholate, deoxycholate, pharmaceutically acceptable salts thereof, analogues thereof, and mixtures or combinations thereof, to form a mixed micellar macromolecular pharmaceutical agent composition.

Each of the micelle-forming compounds, including the alkali metal alkyl sulfate, is in a concentration of from 0.1 to 20 wt./wt. % of the total composition, with the total being less than 50 wt./wt. % of the total composition.

The method can further comprise the step of adding a stabilizer such as a phenolic compound selected from the group phenol, m-cresol and mixtures thereof; the addition of the stabilizer can be either before, during, or after the addition of the alkali metal alkyl sulfate, or before, during or after the addition of the micelle-forming compounds.

The method can further comprise the step of placing the composition into an aerosol dispenser and charging the dispenser with a propellant.

In another specific embodiment, the process comprises:

a) mixing a macromolecular pharmaceutical agent in a suitable solvent with an alkali metal alkyl sulfate, and at least one micelle-forming compound selected from the group consisting of lecithin, hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine, glycerin, polyglycerin, lysine, polylysine, triolein, polydocano alkyl ethers, polidocanol alkyl ethers, chenodeoxycholate, deoxycholate, pharmaceutically acceptable salts thereof, analogues thereof, and mixtures or combinations thereof, to form a first mixed micellar macromolecular pharmaceutical agent composition; and b) adding at least two micelle-forming compounds to the first composition that are different from that added in step a) but selected from the same group.

Again, during or after step a), a stabilizer as described above can be added to the composition. Mixing can be vigorous or not. Vigorous mixing may be accomplished by using high-speed stirrers, such as magnetic stirrers, propeller stirrers, or sonicators, and is preferred.

The present invention also provides a metered dose aerosol dispenser with the composition of the present invention and a propellant contained therein, in which a solution containing the macromolecular pharmaceutical agent and the propellant are in a single phase.

The present invention also provides a method for administering the pharmaceutical compositions of the present invention, by spraying the intermixed composition into the mouth with a metered dose spray device. Application can be to the buccal cavity by spraying into the cavity, without inhalation. It may be necessary or desirable to shake the dispenser prior to spraying the present pharmaceutical composition and propellant into the buccal cavity. The plasma levels and blood glucose levels when orally administering the present insulin-containing compositions are comparable to those achieved when insulin is injected; the present methods offer significant improvements in the quality of life over injection including pain-free and needle-free therapy and improved convenience.

In the case of insulin, which is intended for administration through the mouth cavity, a first micellar solution may be made by adding water or other solvent, and then hydrochloric acid (typically 5M) to powdered insulin, and stirring until the powder is dissolved and a clear solution is obtained. The solution can then neutralized with sodium hydroxide. Other pharmaceutical agents, such as morphine and fentanyl, are water soluble and can be mixed directly with water or other solvent. A sodium alkyl sulfate may be added to the neutralized solution with low speed stirring, either alone or with at least one micelle forming compound. A typical concentration of sodium lauryl sulfate, as the sodium alkyl sulfate, in the aqueous solution is less than about 5 wt./wt. % of the solution. Typically, insulin is present in the micellar solution in an amount which will give a concentration of about 0.1 to 20 wt./wt. % of the final composition.

The solution so formed may then be mixed vigorously, such as by sonication or high speed stirring, to form a micelle solution. Other micelle forming compounds, as described above, may then be added. The mixing may be done with a high-speed mixer or sonicator to ensure uniform micelle particle size distribution within the composition.

In a preferred embodiment, after forming the present micellar pharmaceutical compositions, the phenol and/or m-cresol is added. As indicated above, other ingredients, such as isotonic agents, flavoring agents, anti-oxidants, salts, protease inhibitors or other pharmaceutically acceptable compounds may also be added to an aerosol dispenser. The formulation can be placed in an aerosol dispenser, and the dispenser charged with propellant in a known manner.

The specific concentrations of the above ingredients can be determined by one skilled in the art based upon the general guidelines provided herein. It will be understood that the amounts of certain ingredients may need to be limited in order to avoid compositions which produce foam when sprayed rather than forming a fine spray. For absorption through the oral cavities, it is often desirable to increase, such as by doubling or tripling, the dosage of pharmaceutical agent which is normally required through injection or administration through the gastrointestinal tract.

The desired size of aerosol droplets which are sprayed from the aerosol dispenser will depend, in part, on where the pharmaceutical is to be deposited. For example, for deposition in the lungs, particle sizes of less than about 5 μm are preferred whereas for absorption in the buccal cavity of the mouth, particle sizes of about 5–10 μm are preferred.

The present invention is also directed to a method for enhancing the rate of absorption of a macromolecular pharmaceutical agent comprising administering a composition comprising said agent in conjunction with an alkali metal alkyl sulfate and at least three of the micelle-forming compounds described above. Preferably, this method is carried out by administering directly to the buccal region of the patient.

Administration of the formulation into the buccal cavity, according to any of the present methods, is by spraying the formulation into the mouth, without inhalation, so that the droplets stay in the mouth rather than being drawn into the lungs.

In an additional aspect, the present invention provides a method of administering a pharmaceutical agent to the oral or pulmonary mucosae of a patient comprising: spraying a composition comprising said pharmaceutical agent to said oral or pulmonary mucosae with a metered dose dispenser, such that the pharmaceutical agent is absorbed through said oral or pulmonary mucosae and a peak plasma level of said pharmaceutical agent is obtained in less than about 1 hour. Preferably, the peak plasma level of the pharmaceutical agent is obtained in less than about 45 minutes; most preferably, in less than about 30 minutes. Preferably, the oral mucosae is the buccal mucosa.

The pharmaceutical agent is selected from the group consisting of insulin, heparin, low molecular weight heparin, hirulog, hirugen, huridine, interferons, cytokines, mono and polyclonal antibodies, immunoglobins, chemotherapeutic agents, vaccines, glycoproteins, bacterial toxoids, hormones, calcitonins, glucagon like peptides, antibiotics, thrombolytic compounds, platelet inhibitors, DNA, RNA, gene therapeutics, antisense oligonucleotides, hypnotics and steroids. Preferably, the pharmaceutical agent is insulin.

As used herein, the term "peak plasma level" refers to the highest amount of pharmaceutical agent measured in the blood, plus or minus about 10%.

In yet a further aspect, the present invention provides a method of administering a pharmaceutical agent to the oral mucosae of a patient comprising: spraying a composition comprising said pharmaceutical agent to said oral mucosae with a metered dose dispenser, such that the pharmaceutical agent is absorbed through the oral mucosae and a peak plasma level of said pharmaceutical agent is obtained in less than about 1 hour. Preferably, the peak plasma level of the pharmaceutical agent is obtained in less than about 45 minutes; most preferably, in less than about 30 minutes. Preferably, the oral mucosae is the buccal mucosae.

The pharmaceutical agent is selected from the group consisting of insulin, heparin, low molecular weight heparin, hirulog, hirugen, huridine, interferons, cytokines, mono and polyclonal antibodies, immunoglobins, chemotherapeutic agents, vaccines, glycoproteins, bacterial toxoids, hormones, calcitonins, glucagon like peptides, antibiotics, thrombolytic compounds, platelet inhibitors, DNA, RNA, gene therapeutics, antisense oligonucleotides, hypnotics, opioids, narcotics, pain killers and steroids. Preferably, the pharmaceutical agent is insulin, morphine or fentanyl.

In an additional aspect, the present invention provides a method of enhancing absorption of a pharmaceutical agent administered to the oral or pulmonary mucosae of a patient comprising: spraying a composition comprising said pharmaceutical agent to said oral or pulmonary mucosae with a metered dose dispenser, such that the pharmaceutical agent is absorbed through said oral or pulmonary mucosae and a peak plasma level of said pharmaceutical agent is obtained in less than about 1 hour. Preferably, the peak plasma level of the pharmaceutical agent is obtained in less than about 45 minutes; most preferably, in less than about 30 minutes. Preferably, the oral mucosae is the buccal mucosa.

The pharmaceutical agent is selected from the group consisting of insulin, heparin, low molecular weight heparin, hirulog, hirugen, huridine, interferons, cytokines, mono and polyclonal antibodies, immunoglobins, chemotherapeutic agents, vaccines, glycoproteins, bacterial toxoids, hormones, calcitonins, glucagon like peptides, antibiotics, thrombolytic compounds, platelet inhibitors, DNA, RNA, gene therapeutics, antisense oligonucleotides, hypnotics and steroids. Preferably, the pharmaceutical agent is insulin.

In yet a further aspect, the present invention provides a method of enhancing absorption of a pharmaceutical agent administered to the oral mucosae of a patient comprising: spraying a composition comprising said pharmaceutical agent to said oral mucosae with a metered dose dispenser, such that the pharmaceutical agent is absorbed through the oral mucosae and a peak plasma level of said pharmaceutical agent is obtained in less than about 1 hour. Preferably, the peak plasma level of the pharmaceutical agent is obtained in less than about 45 minutes; most preferably, in less than about 30 minutes. Preferably, the oral mucosae is the buccal mucosae.

The pharmaceutical agent is selected from the group consisting of insulin, heparin, low molecular weight heparin, hirulog, hirugen, huridine, interferons, cytokines, mono and polyclonal antibodies, immunoglobins, chemotherapeutic agents, vaccines, glycoproteins, bacterial toxoids, hormones, calcitonins, glucagon like peptides, antibiotics, thrombolytic compounds, platelet inhibitors, DNA, RNA, gene therapeutics, antisense oligonucleotides, hypnotics, opioids, narcotics, pain killers and steroids. Preferably, the pharmaceutical agent is insulin, morphine or fentanyl.

EXAMPLES

The following examples are intended to illustrate the invention, and should not be considered as limiting the invention in any way.

Example 1

About 100 mg of powdered insulin were placed in a glass beaker equipped with a stirrer. Ten ml of distilled water were added and the solution was stirred at low speed. To this solution was added 5M HCl (pH 2) solution dropwise until the insulin was solubilized completely. This solution was then neutralized, while stirring slowly, with 5M NaOH solution dropwise until the pH was between about 7 and 8. To this solution was added 50 mg sodium lauryl sulfate, 36 mg deoxycholate, 50 mg trihydroxy oxocholanyl glycine (sodium glycocholate) and 20 mg dibasic Na phosphate; the compounds were dissolved completely. 250 mg glycerin were then added while stirring at high speed, i.e. 2000 rpm. The solution was stirred for 30 minutes and then stored at 10° C. To this mixture 40 mg m-cresol and 40 mg phenol were added. Chenodeoxycholate or polyoxyethylene ethers can be used in place of the deoxycholate.

The solution was pipetted (1 ml/vial) into 10 ml capacity glass vials. The vials were charged with HFA-134a propellant and stored at room temperature.

Insulin absorption efficacy methods were used to test this formulation on several diabetic patients. Ten diabetic volunteers were asked to fast overnight and not have any breakfast prior to dosing. The patients were challenged with a high calorie meal after the insulin dose. Blood glucose levels were measured for the next 4 hours. Results are shown in Table 1. On day one, patients were given placebo puffs and an oral hypoglycemic agent (Metformin, "Tablets"); on day two, patients were given a 70 unit dose of oral insulin prepared as described above; and on day three, patients were given a 70 unit dose of the present oral insulin composition. As seen in Table 1, the present oral insulin compositions performed much better than the oral hypoglycemic agents in controlling glucose levels.

TABLE 1

| Placebo + Tablets Day-1 | Oral-70 Day-2 | Oral-70-2 Repeat dose Day-3 |
|---|---|---|
| 6.8 | 6.4 | 6.6 |
| 7.0 | 6.1 | 6.3 |
| 7.8 | 6.5 | 7.1 |
| 12.2 | 8.6 | 8.9 |
| 11.3 | 9.0 | 9.1 |
| 10.7 | 8.1 | 8.3 |
| 10.1 | 7.4 | 7 |
| 9.0 | 6.4 | 6.1 |
| 8.4 | 6.1 | 5.8 |
| 8.2 | 5.5 | 5.3 |

The procedure was repeated with the following results:

TABLE 2

| Placebo + Tablets Day-1 | Oral-70 Day-2 | Oral-70-2 Repeat dose Day-3 |
|---|---|---|
| 6.3 | 5.9 | 6.2 |
| 6.7 | 5.4 | 5.9 |
| 7.5 | 6.0 | 6.7 |
| 10.5 | 8.4 | 8.4 |
| 10.3 | 8.2 | 8.4 |
| 9.1 | 6.8 | 7.2 |
| 8.0 | 5.8 | 5.9 |
| 6.9 | 5.3 | 5.3 |
| 6.4 | 5.1 | 5.2 |
| 6.1 | 4.7 | 4.7 |

Example 2

An insulin solution was prepared as described in Example 1. To this solution was added 7 mg sodium lauryl sulfate, 7 mg polyoxyethylene ether (10 lauryl) and 7 mg trihydroxy oxo cholanyl glycine and dissolved completely. Seven mg lecithin, solubilized in a water alcohol solution (7 mg/mL) were then added while stirring at high speed, i.e. 2000 rpm. The solution was stirred for 30 minutes and then stored at 10° C. The resulting mixed micellar solution had about 200 units insulin. To this mixture 5 mg phenol, 5 mg m-cresol and 10 mg glycerin were added.

The solution was pipetted (1 mL/vial) into 10 mL capacity glass vials. The vials were then charged with HFA-134a propellant with a Pamasol 2008 automatic gas filling apparatus. The amount of propellant was adjusted to 9 mL shot size in order to deliver 2 units insulin per actuation of the aerosol vial. The valves of the vials were designed to deliver 100 μL spray per actuation, containing 2 units insulin. The formulation in the glass vial, including the propellant, was in a single phase, i.e. was homogeneous.

The aerodynamic particle size was determined by an 8-stage USP Anderson® Cascade Impactor Mark II. The impactor was cleaned with methanol and air dried at 30° C. Glass fibre filters were placed on the collection plates. The actuator was attached to the mouthpiece of the impactor and assembled onto the USP induction port and jet stages. A vacuum pump was connected and the air flow rate set to 28.3 liters per minute. The vial was primed by shaking for 10 seconds and actuated twice to waste. The shot was delivered by discharging the actuator into the mouthpiece and repeating 25 times. The deposited insulin was collected by rinsing the mouthpiece with 0.6 mL EDTA in 10 mL water at pH 8.7. The filters were removed and placed in scintillation vials and sonicated for 15 minutes. The quantity of insulin was then analyzed using RP-HPLC. The results are shown in Table 3 (2 units per actuation) and 4 (4 units per actuation).

TABLE 3

| Stage No. | 0 | 1 | 2 | 3 |
|---|---|---|---|---|
| Volume (mL) | 10 | 10 | 10 | 10 |
| Mass (mg) | 0.79 | 0.81 | 0.78 | * |
| Units | 10.4 | 10.0 | 10.0 | |
| Actuation | 5 | 5 | 5 | |
| Units per actuation | 2.0 | 2.0 | 2.1 | |
| Particle size (μm) | 8.8 | 5.8 | 5.7 | |

*not determined/detected

TABLE 4

| Stage No. | 0 | 1 | 2 | 3 |
|---|---|---|---|---|
| Volume (mL) | 10 | 10 | 10 | 10 |
| Mass (mg) | 0.79 | 0.81 | 0.78 | ** |
| Units | 20.7 | 21.0 | 20.1 | |
| Actuation | 5 | 5 | 5 | |
| Units per actuation | 4.15 | 4.18 | 4.01 | |
| Particle size (μm) | 9 | 5.8 | 4.7 | |

**not determined

Based on these tests, the average particle size was determined to be about 7 μm, and stages 3–8, not all of which are shown, revealed no insulin deposition, indicating that most particles were larger than about 6 μm. This suggests that there would be no deep lung deposition of the formulation and that most of the formulation would be deposited in the buccal cavity.

Further tests were conducted to determine the shot size accuracy, by firing shots into thiel tubes and weighing the tubes before and after the sample collection. The tests showed the shots for 2 units per actuation weighed between 0.075 and 0.083 grams, i.e. within about ±5%. The tests showed the shots for 4 units per actuation weighed between 0.076 and 0.083 grams, i.e. within about ±5%. The tests showed the shots for 6 units per actuation weighted between 0.070 and 0.082 grams, i.e. within about ±8%. HPLC analysis showed the doses delivered to be from 2.01 units to 2.07 units for 2 units per actuation, from 3.9 units to 4.4 units for 4 units per actuation, and from 5.8 units to 6.3 units for 6 units per actuation.

Ten diabetic volunteers were asked to fast overnight and not have any breakfast prior to dosing. On the first day, the volunteers were given 10 units insulin by injection (regular fast acting insulin, obtained from Eli Lilly). On the second day, the volunteers were given 60 units insulin of this example (10 puffs of 6 units each) into the mouth, without inhalation. Plasma insulin levels were measured at intervals by the RIA method for 3 hours. The average results, in micromoles per ml, are shown in Table 5. Blood glucose levels were also monitored at intervals using Bayer's glucometer Elite for 3 hours. The average results, in millimoles per liter, are shown in Table 6.

TABLE 5

| Time*: | 0 | 15 | 30 | 45 | 60 | 90 | 120 | 150 | 180 |
|---|---|---|---|---|---|---|---|---|---|
| Injection: | 10 | 9.1 | 11 | 16 | 31 | 45 | 32 | 25 | 20 |
| Spray: | 8.7 | 12.1 | 19.8 | 28 | 27 | 36 | 29 | 21 | 13 |

*time in minutes

This test indicated that the direct insulin injection method and the spray method for delivering the present compositions resulted in comparable plasma insulin levels.

TABLE 6

| Time*: | 0 | 15 | 30 | 45 | 60 | 90 | 120 | 150 | 180 |
|---|---|---|---|---|---|---|---|---|---|
| Injection: | 6.1 | 6.0 | 5.9 | 5.5 | 5.1 | 4.5 | 3.8 | 4.2 | 4.4 |
| Spray: | 6.6 | 6.3 | 5.8 | 5.2 | 4.8 | 4.9 | 4.5 | 5.0 | 5.3 |

*time in minutes

This test indicated that the direct insulin injection method and the spray method for delivering the present compositions resulted in comparable blood glucose level.

Tests were also conducted with 40 units of spray at 10 puffs each, and compared to 10 units injected by measuring plasma levels and glucose levels as above. The results are shown in Table 7 (plasma) and 8 (glucose).

TABLE 7

| Time*: | 0 | 15 | 30 | 45 | 60 | 90 | 120 | 150 | 180 |
|---|---|---|---|---|---|---|---|---|---|
| Injection: | 9 | 9 | 13 | 19 | 34 | 45 | 42 | 35 | 24 |
| Spray: | 10 | 13 | 18.5 | 27 | 30 | 33 | 29 | 19 | 14 |

*time in minutes

This test indicated that the direct insulin injection method and the spray method for delivering the present compositions resulted in comparable plasma insulin.

TABLE 8

| Time*: | 0 | 15 | 30 | 60 | 90 | 120 | 150 | 180 |
|---|---|---|---|---|---|---|---|---|
| Injection: | 5.8 | 6.0 | 5.9 | 5.5 | 5.0 | 4.5 | 4.1 | 3.9 |
| Spray: | 6.0 | 5.7 | 5.4 | 5.0 | 5.1 | 4.7 | 4.5 | 4.2 |

*time in minutes

This test indicated that the direct insulin injection method and the spray method for delivering the present compositions resulted in comparable glucose levels.

Example 3

An insulin solution was prepared as described in Example 1. To this solution was added 30.4 mg sodium lauryl sulfate per ml of insulin solution, 30.4 mg polidocanol 9 lauryl ether per ml of insulin solution and 10.0 mg polylysine per ml of insulin solution, and the compounds dissolved completely. 15.2 mg triolein per ml of insulin solution was then added while stirring at high speed, i.e. 2000 rpm. The solution was stirred for 30 minutes and then stored at 10° C. The resulting solution was a mixed micellar solution. To this mixture 15.2 mg m-cresol per ml of insulin solution were added.

The solution was pipetted (1 mL) into glass vials. The vials were then charged with 10.8 g HFA 134a propellant per vial, with a Pamasol® 2008 automatic gas filling apparatus. The valves of the vials were designed to deliver 100 µL spray per actuation, containing 6 units insulin. The formulation in the glass vial including the propellant, was in a single phase, i.e. was homogeneous.

Ten diabetic volunteers were asked to fast overnight and not have any breakfast prior to dosing. On the first day, the volunteers were given 10 units insulin by injection. On the second day, the volunteers were given 60 units insulin of this example (10 puffs of 6 units each) into the mouth, without inhalation. Plasma insulin levels were measured at intervals by the RIA method for 3 hours. The average results, in micromoles per ml, are shown in Table 9. Blood glucose levels were also monitored at intervals using Bayer's glucometer Elite for 3 hours. The average results, in millimoles per liter, are shown in Table 10.

TABLE 9

| Time*: | 0 | 15 | 30 | 45 | 60 | 90 | 120 | 150 | 180 |
|---|---|---|---|---|---|---|---|---|---|
| Injection: | 9 | 9.1 | 14 | 20 | 40 | 48 | 39 | 34 | 27 |
| Spray: | 10 | 15.1 | 22 | 32 | 47 | 36 | 27 | 21 | 19 |

*time in minutes

This test indicated that the direct insulin injection method and the spray method for delivering the present compositions resulted in comparable plasma insulin levels.

TABLE 10

| Time*: | 0 | 15 | 30 | 45 | 60 | 90 | 120 | 150 | 180 |
|---|---|---|---|---|---|---|---|---|---|
| Injection: | 6.6 | 6.5 | 6.1 | 5.5 | 4.9 | 4.5 | 3.8 | 3.5 | 4.4 |
| Spray: | 6.8 | 5.9 | 5.2 | 4.8 | 4.3 | 3.9 | 4.5 | 5.7 | 5.3 |

*time in minutes

This test indicated that the direct insulin injection method and the spray method for delivering the present compositions resulted in comparable glucose levels.

Example 4

An insulin solution was prepared as described in Example 1. The solution was diluted with distilled water until there were 600 units insulin per ml of solution. One ml portions were then transferred to 10 mL capacity glass vials, which were then charged with 10.8 g HFA 134a propellant using a Pamasol® 2008 semi-automatic gas filling apparatus.

The gas phase and the aqueous phase were observed to be distinctly separate. Even shaking of the vials did not appear to homogenize the composition.

Tests were conducted to determine the shot size accuracy, by firing shots into thiel tubes and weighing the tubes before and after the sample collection. The tests showed five consecutive shots for 6 units per actuation weighed 0.094, 0.110, 0.200, 0.150 and 0.050 grams, i.e. within about ±60% of the average. This compares with ±8% in Example 2 (which describes a composition within the scope of the present invention).

HPLC analysis showed the average doses delivered to be 5.4 units per actuation from shots 5–10, 7.1 units per actuation from shots 45–50 and 8.6 units per actuation from shots 85–90.

These results showed that uniform dose delivery is achievable with the micelle-forming ingredients of the present invention, but not without, based upon the results of this Example as compared with the results of Example 2.

Example 5

Ten ml of concentrated insulin containing 10,000 units per ml were placed in a glass beaker. To this solution was added 7 mg sodium lauryl sulfate, 7 mg polyoxyethylene ether (10 lauryl), 7 mg trihydroxy oxocholanyl glycine and 7 mg lecithin. The components were stirred until they were completely dissolved. Seven mg phenol and 7 mg m-cresol were added to the solution and mixed thoroughly.

One ml portions of the solution were pipetted into 10 mL capacity glass vials. The vials had metered dose valves thereon. The vials were then charged with HFA 134a propellant with Pamasol® 2008 gas filling apparatus. The amount of propellant was adjusted to 9 mL per vial in order to deliver 10 units of insulin per actuation of the valve (100 µL shot/actuation). The formulation, in the glass vial, including the propellant, was in a single phase, i.e. was homogeneous.

Ten diabetic human patients fasted overnight and did not have a breakfast prior to dosing. On the first day, each patient had 7 units regular fast acting insulin, obtained from Eli Lilly, administered by injection. On the second day, each patient was given 70 units of the insulin formulation of this Example (7 puffs of 10 unit each) into the mouth, without inhalation. Blood samples were collected and plasma glucose levels were measured at intervals using Bayer's glucometer Elite for 3 hours. The average results, in millimoles per ml, are shown in Table 11. Insulin levels were also monitored at intervals by the RIA method for 3 hours. The average results, in micromoles per liter, are shown in Table 12.

TABLE 11

| Time*: | 0 | 15 | 30 | 45 | 60 | 90 | 120 | 150 | 180 |
|---|---|---|---|---|---|---|---|---|---|
| Injection: | 6.5 | 6.3 | 5.7 | 5.2 | 4.8 | 4.9 | 3.8 | 4.5 | 4.7 |
| Spray: | 6.1 | 6.0 | 6.0 | 5.9 | 5.5 | 4.5 | 3.6 | 4.1 | 4.4 |

TABLE 12

| Time*: | 0 | 15 | 30 | 45 | 60 | 90 | 120 | 150 | 180 |
|---|---|---|---|---|---|---|---|---|---|
| Injection: | 8.7 | 12.1 | 19.8 | 29.0 | 36.0 | 37.0 | 33.0 | 23.0 | 14.0 |
| Spray: | 9.1 | 11.0 | 16.0 | 31.0 | 45.0 | 43.0 | 45.0 | 32.0 | 22.0 |

*time in minutes

This test indicated that the direct insulin injection method and the spray method of administering the present compositions resulted in comparable insulin levels.

Example 6

Ten ml of concentrated insulin containing 10,000 units per ml were placed in a glass beaker. To this solution was added 15 mg sodium lauryl sulfate, 15 mg chenodeoxycholate, 15 mg trihydroxy oxocholanyl glycine and 7 mg lecithin. The components were stirred until they were completely dissolved. Seven mg phenol and 7 mg m-cresol were added to the solution and mixed thoroughly.

One ml portions of the solution were pipetted into 10 mL capacity glass vials. The vials had metered dose valves thereon. The vials were then charged with HFA 134a propellant with Pamasol® 2008 gas filling apparatus. The amount of propellant was adjusted to 9 mL per vial in order to deliver 10 units of insulin per actuation of the valve (100 µL shot/actuation). The formulation, in the glass vial, including the propellant, was in a single phase, i.e. was homogeneous.

Ten diabetic patients fasted overnight and did not have a breakfast prior to dosing. On the first day, each patient had 7 units regular fast acting insulin, obtained from Eli Lilly, administered by injection. Fifteen minutes after administering the insulin, each patient was given a 250-calorie Sustacal® drink, which was consumed within 10 minutes. On the second day, each patient was given 70 units insulin of this example (7 puffs of 10 units each) into the mouth, without inhalation. Fifteen minutes after administering the insulin, each patient was given a 250-calorie Sustacal® drink, which was consumed within 10 minutes. Blood samples were collected and plasma glucose levels were measured at intervals, using Bayer's glucometer Elite for 4 hours. The average results, in millimoles per ml, are shown in Table 13.

TABLE 13

| Time*: | 0 | 15 | 30 | 60 | 90 | 120 | 150 | 180 |
|---|---|---|---|---|---|---|---|---|
| Injection: | 9.2 | 9.0 | 9.5 | 12.3 | 12.4 | 12.6 | 11.3 | 9.7 |
| Spray: | 8.8 | 8.8 | 8.7 | 10.4 | 12.0 | 12.4 | 11.9 | 10.5 |

*time in minutes

These tests indicated that the direct insulin injection method and the spray method for administering the present compositions resulted in comparable blood glucose levels.

Example 7

An additional embodiment of the invention was prepared, using the methods described above. An insulin solution was prepared as described in Example 1, with the following additional ingredients and amounts:

| | |
|---|---|
| glycerin | 250 mg |
| phenol | 30 mg |
| Na deoxycholate | 30 mg |
| Na lauryl sulfate | 40 mg |
| Na glycocholate | 60 mg |

Figure 1:
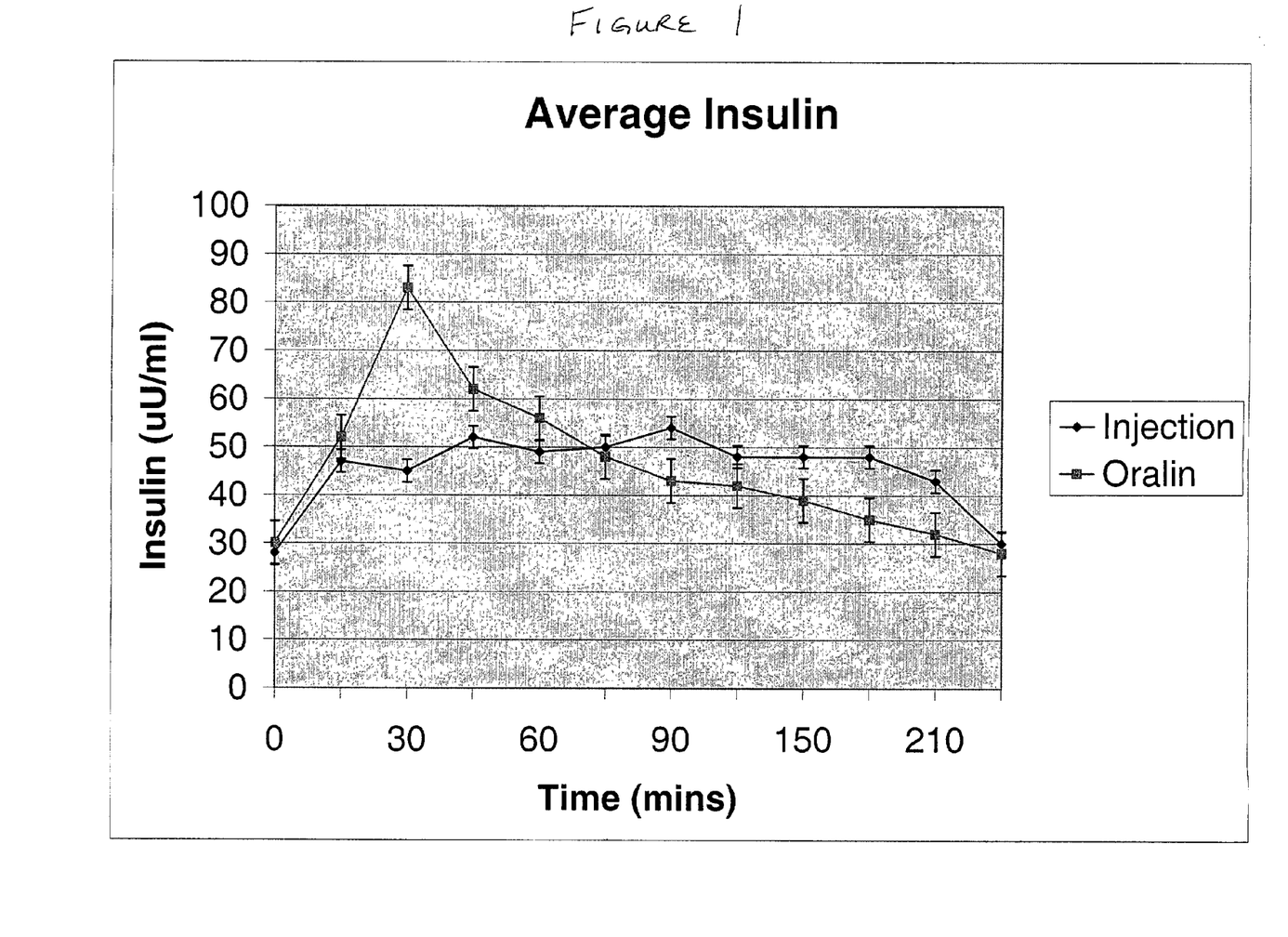
FIG. 1 compares plasma insulin levels obtained from injection and oral administration using the methods of the present invention, in Type-1 diabetics.
Figure 2:
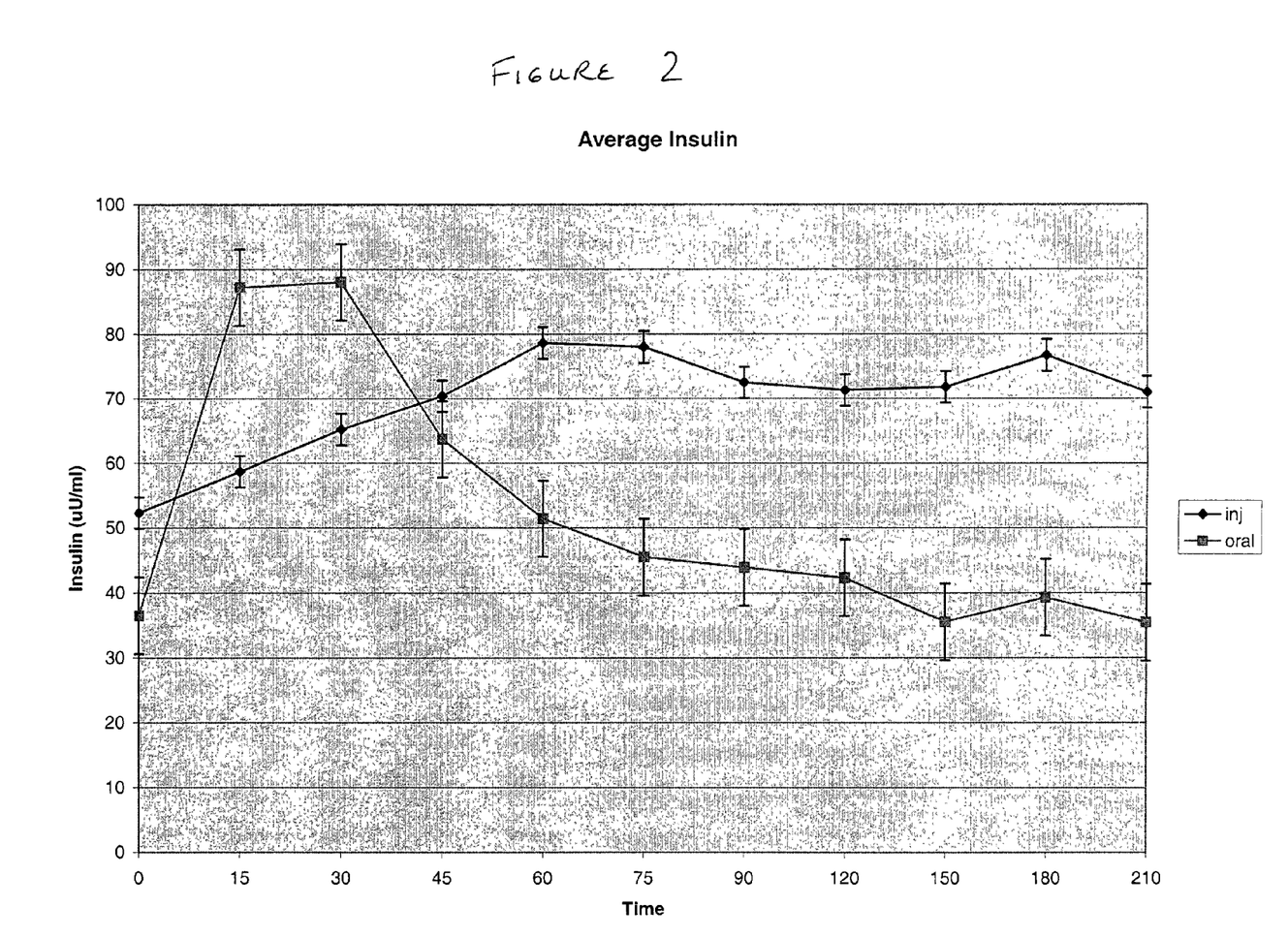
FIG. 2 compares plasma insulin levels obtained from injection and oral administration using the methods of the present invention, in Type-2 diabetics.

Tests were conducted on this composition, administered to the buccal region of the oral mucosae with a metered dose dispenser, to determine peak plasma levels of the pharmaceutical agent as compared with injection. Data is presented in tabular form in Table 1 (below), and in graphical form in FIGS. 1 and 2. As can be seen in FIGS. 1 (peak plasma levels of the composition in Type-2 diabetics) and 2 (peak plasma levels of the composition in Type-1 diabetics), peak plasma levels were obtained in about 30 minutes or less. These results indicate that rapid absorption can be achieved in a pain-free therapy.

TABLE 1

Insulin Levels-Oral Insulin
Free Insulin Levels uU/mL

| Patient # | −30 | 0 | 15 | 30 | 45 | 60 | 90 | 120 | 180 | 240 |
|---|---|---|---|---|---|---|---|---|---|---|
| RPG001 | 34.4 | 24.3 | 121.9 | 99.7 | 73.1 | 39.8 | 21.5 | 27.4 | 22.8 | 24.2 |
| LAB002 | 14.2 | 34.8 | 27.2 | 16.9 | 22 | 23.2 | 20.7 | 18.7 | 14.6 | 17.3 |
| CLT003 | 11.5 | 37 | 154.3 | 62 | 44.2 | 37.3 | 31.2 | 29 | 19.6 | 19.9 |
| JLF004 | 25.7 | 55.1 | 66.6 | 61.3 | 53.3 | 49.9 | 29.5 | 29.1 | 29.5 | |
| KDM005 | 15.8 | 16.3 | 14.4 | 9.2 | 13 | 14.1 | 17 | 16.5 | 21.2 | 24.2 |
| KCL006 | 37.4 | 45.5 | 48 | 37.2 | 36.6 | 37.3 | 36.3 | 32.4 | 36 | |
| MWR007 | 14.8 | 19.2 | 21.9 | 20.3 | 21.3 | 21.1 | 25.6 | 24.3 | 22.1 | 20.9 |
| LSL008 | | | | | | | | | | |
| JFK009 | 16.9 | 22.8 | 27.5 | 22.9 | 28.2 | 16.6 | 17.4 | 19.1 | 19.7 | 21.5 |
| MEAN | 22.0 | 33.2 | 64.9 | 43.8 | 37.6 | 31.8 | 26.0 | 25.3 | 23.7 | 21.3 |

Example 8

An additional embodiment of the invention was prepared, using the methods generally as described above. A fentanyl solution was prepared by dissolving fentanyl citrate powder in water, and adding the following additional ingredients and amounts:

| | |
|---|---|
| Fentanyl Citrate | 0.5 mg |
| Polyoxyethylene-9-Lauryl Ether | 45 mg |
| Glycerin | 60 mg |
| Phenol | 50 mg |
| Sodium Lauryl Sulfate | 40 mg |
| Sodium Glycocholate | 30 mg |
| Ethanol | 0.20 ml |
| Water for Injection | Approximately 1 ml |
| HFA 134A (propellant) | 10.0 g |

Figure 3:
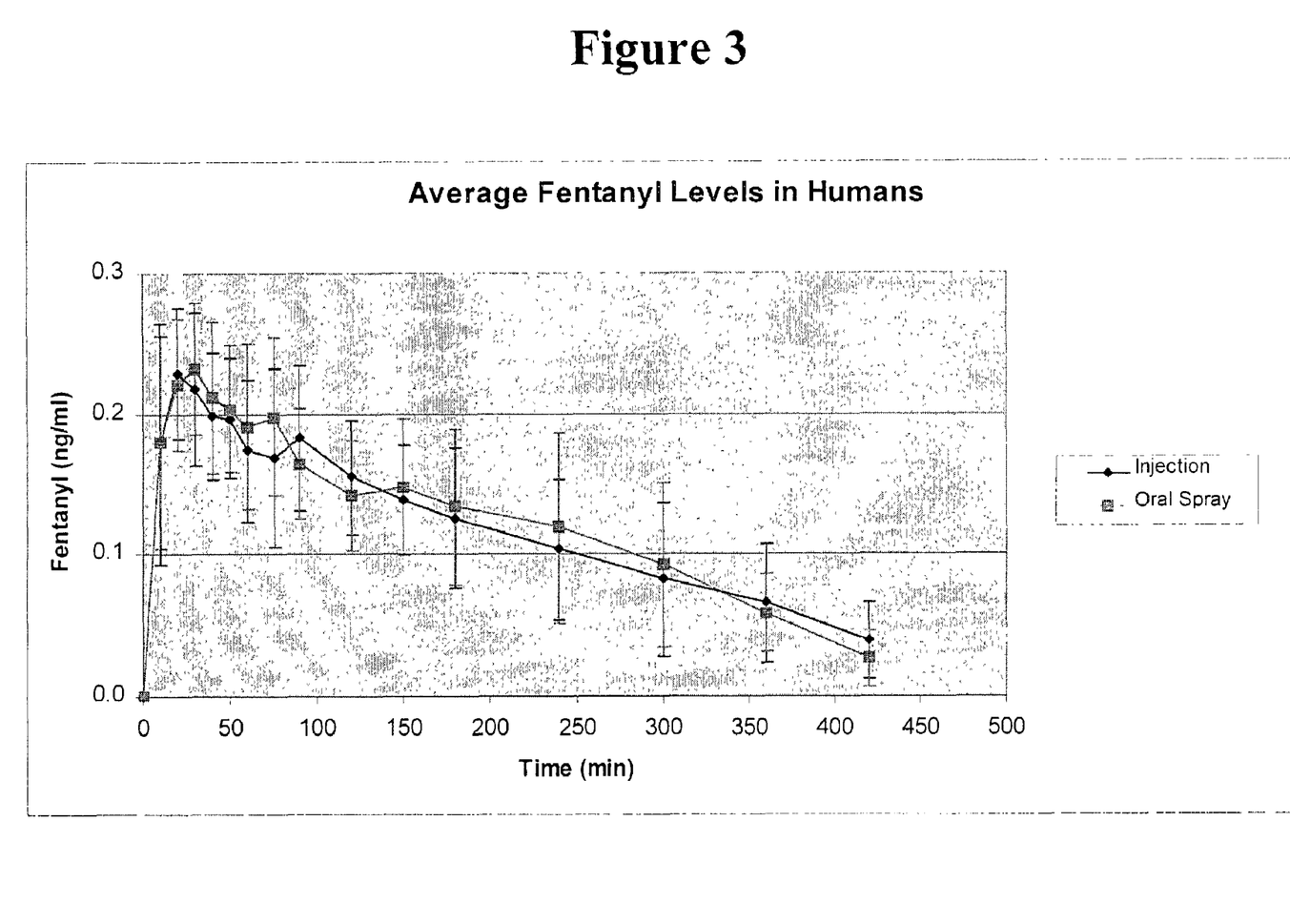
FIG. 3 compares plasma fentanyl levels obtained from injection and oral administration using the methods of the present invention.

Tests were conducted on this composition, administered to the buccal region of the oral mucosae with a metered dose dispenser, to determine peak plasma levels of the fentanyl as compared with injection. Data is presented in tabular form in Table 3 (below), and in graphical form in FIG. 3.

TABLE 3

Injection

| SAMPLE | TIME (min) | CG-10 (ng/ml) | GA-02 (ng/ml) | JS-003 (ng/ml) | CA-004 (ng/ml) | DD-05 (ng/ml) | MD-06 (ng/ml) | MB-07 (ng/ml) | CV-08 (ng/ml) | MN-09 (ng/ml) | AM-010 (ng/ml) |
|---|---|---|---|---|---|---|---|---|---|---|---|
| 1 | 0 | 0.000 | 0.000 | 0.000 | 0.000 | 0.000 | 0.000 | 0.000 | 0.000 | 0.000 | 0.000 |
| 2 | 10 | 0.197 | 0.022 | 0.007 | 0.194 | 0.320 | 0.114 | 0.250 | 0.224 | 0.189 | 0.166 |
| 3 | 20 | 0.198 | 0.160 | 0.308 | 0.236 | 0.205 | 0.237 | 0.194 | 0.269 | 0.216 | 0.298 |
| 4 | 30 | 0.181 | 0.190 | 0.316 | 0.128 | 0.168 | 0.214 | 0.263 | 0.196 | 0.292 | 0.271 |
| 5 | 40 | 0.177 | 0.153 | 0.243 | 0.120 | 0.225 | 0.139 | 0.253 | 0.188 | 0.246 | 0.220 |
| 6 | 50 | 0.228 | 0.226 | 0.212 | 0.187 | 0.158 | 0.168 | 0.289 | 0.189 | 0.217 | 0.198 |
| 7 | 60 | 0.071 | 0.122 | 0.194 | 0.218 | 0.163 | 0.147 | 0.283 | 0.187 | 0.164 | 0.159 |
| 8 | 75 | 0.039 | 0.149 | 0.190 | 0.196 | 0.207 | 0.108 | 0.326 | 0.175 | 0.136 | 0.158 |
| 9 | 90 | 0.155 | 0.330 | 0.177 | 0.155 | 0.113 | 0.198 | 0.253 | 0.172 | 0.176 | 0.154 |
| 10 | 120 | 0.108 | 0.243 | 0.119 | 0.201 | 0.174 | 0.120 | 0.209 | 0.161 | 0.154 | 0.130 |
| 11 | 150 | 0.087 | 0.197 | 0.103 | 0.126 | 0.218 | 0.164 | 0.117 | 0.129 | 0.152 | 0.128 |
| 12 | 180 | 0.090 | 0.100 | 0.110 | 0.085 | 0.226 | 0.217 | 0.063 | 0.129 | 0.085 | 0.100 |
| 13 | 240 | 0.020 | 0.165 | 0.082 | 0.056 | 0.142 | 0.208 | 0.075 | 0.123 | 0.064 | 0.114 |
| 14 | 300 | 0.146 | 0.047 | 0.062 | 0.036 | 0.154 | 0.219 | 0.026 | 0.073 | 0.020 | 0.099 |
| 15 | 360 | 0.112 | 0.022 | 0.059 | 0.043 | 0.153 | 0.133 | 0.001 | 0.041 | 0.022 | 0.094 |
| 16 | 420 | 0.051 | 0.080 | 0.053 | 0.021 | 0.016 | 0.089 | 0.001 | 0.017 | 0.026 | 0.051 |

| SAMPLE | JB 11 (ng/ml) | DZ-12 (ng/ml) | ML-13 (ng/ml) | LM-14 (ng/ml) | ST-15 (ng/ml) | IJ-16 (ng/ml) | Mean | Std. Dev. | SEM | CV |
|---|---|---|---|---|---|---|---|---|---|---|
| 1 | 0.000 | 0.000 | 0.000 | 0.000 | 0.000 | 0.000 | 0.000 | 0.000 | 0.000 | 0.000 |
| 2 | 0.251 | 0.115 | 0.267 | 0.193 | 0.113 | 0.237 | 0.179 | 0.086 | 0.022 | 0.482 |
| 3 | 0.249 | 0.187 | 0.201 | 0.202 | 0.184 | 0.311 | 0.228 | 0.047 | 0.012 | 0.205 |
| 4 | 0.177 | 0.192 | 0.157 | 0.283 | 0.249 | 0.202 | 0.217 | 0.055 | 0.014 | 0.251 |
| 5 | 0.126 | 0.193 | 0.181 | 0.235 | 0.232 | 0.240 | 0.198 | 0.045 | 0.011 | 0.227 |
| 6 | 0.112 | 0.227 | 0.123 | 0.194 | 0.220 | 0.199 | 0.197 | 0.043 | 0.011 | 0.218 |
| 7 | 0.143 | 0.250 | 0.128 | 0.196 | 0.162 | 0.188 | 0.173 | 0.051 | 0.013 | 0.292 |
| 8 | 0.135 | 0.248 | 0.137 | 0.148 | 0.199 | 0.140 | 0.168 | 0.063 | 0.016 | 0.376 |
| 9 | 0.166 | 0.229 | 0.182 | 0.145 | 0.179 | 0.134 | 0.182 | 0.052 | 0.013 | 0.285 |

TABLE 3-continued

| 10 | 0.178 | 0.135 | 0.180 | 0.132 | 0.095 | 0.133 | 0.155 | 0.041 | 0.010 | 0.263 |
| 11 | 0.186 | 0.105 | 0.162 | 0.127 | 0.081 | 0.134 | 0.139 | 0.039 | 0.010 | 0.281 |
| 12 | 0.203 | 0.106 | 0.153 | 0.124 | 0.091 | 0.119 | 0.125 | 0.050 | 0.012 | 0.396 |
| 13 | 0.136 | 0.102 | 0.158 | 0.046 | 0.079 | 0.081 | 0.103 | 0.050 | 0.012 | 0.482 |
| 14 | 0.094 | 0.089 | 0.089 | 0.023 | 0.056 | 0.081 | 0.082 | 0.054 | 0.013 | 0.656 |
| 15 | 0.088 | 0.062 | 0.043 | 0.060 | 0.045 | 0.067 | 0.065 | 0.041 | 0.010 | 0.634 |
| 16 | 0.038 | 0.032 | 0.075 | 0.003 | 0.022 | 0.052 | 0.039 | 0.027 | 0.007 | 0.682 |

Oral Spray

| SAMPLE | TIME (min) | CG-01 (ng/ml) | GA-02 (ng/ml) | JS-003 (ng/ml) | CA-004 (ng/ml) | DD-05 (ng/ml) | MD-06 (ng/ml) | MB-07 (ng/ml) | CV-08 (ng/ml) | MN-09 (ng/ml) | AM-010 (ng/ml) |
|---|---|---|---|---|---|---|---|---|---|---|---|
| 1 | 0 | 0.000 | 0.000 | 0.000 | 0.000 | 0.000 | 0.000 | 0.000 | 0.000 | 0.000 | 0.000 |
| 2 | 10 | 0.170 | 0.145 | 0.058 | 0.050 | 0.350 | 0.119 | 0.272 | 0.235 | 0.197 | 0.142 |
| 3 | 20 | 0.198 | 0.182 | 0.282 | 0.242 | 0.239 | 0.208 | 0.148 | 0.309 | 0.265 | 0.279 |
| 4 | 30 | 0.218 | 0.221 | 0.339 | 0.168 | 0.238 | 0.242 | 0.216 | 0.222 | 0.272 | 0.233 |
| 5 | 40 | 0.232 | 0.166 | 0.255 | 0.132 | 0.250 | 0.158 | 0.269 | 0.214 | 0.302 | 0.225 |
| 6 | 50 | 0.265 | 0.144 | 0.227 | 0.166 | 0.164 | 0.170 | 0.299 | 0.175 | 0.266 | 0.220 |
| 7 | 60 | 0.100 | 0.129 | 0.185 | 0.222 | 0.144 | 0.197 | 0.375 | 0.168 | 0.175 | 0.202 |
| 8 | 75 | 0.198 | 0.312 | 0.181 | 0.232 | 0.156 | 0.116 | 0.333 | 0.159 | 0.181 | 0.197 |
| 9 | 90 | 0.162 | 0.235 | 0.105 | 0.124 | 0.161 | 0.146 | 0.217 | 0.155 | 0.112 | 0.164 |
| 10 | 120 | 0.145 | 0.157 | 0.106 | 0.023 | 0.135 | 0.181 | 0.179 | 0.135 | 0.110 | 0.162 |
| 11 | 150 | 0.184 | 0.142 | 0.109 | 0.135 | 0.301 | 0.197 | 0.126 | 0.132 | 0.128 | 0.141 |
| 12 | 180 | 0.153 | 0.102 | 0.098 | 0.092 | 0.303 | 0.209 | 0.103 | 0.130 | 0.127 | 0.103 |
| 13 | 240 | 0.215 | 0.091 | 0.075 | 0.078 | 0.281 | 0.242 | 0.125 | 0.109 | 0.087 | 0.071 |
| 14 | 300 | 0.180 | 0.027 | 0.082 | 0.056 | 0.240 | 0.167 | 0.101 | 0.095 | 0.054 | 0.078 |
| 15 | 360 | 0.110 | 0.053 | 0.047 | 0.023 | 0.088 | 0.068 | 0.075 | 0.092 | 0.017 | 0.077 |
| 16 | 420 | 0.041 | 0.007 | 0.035 | 0.014 | 0.014 | 0.055 | 0.026 | 0.014 | 0.028 | 0.056 |

| SAMPLE | JB 11 (ng/ml) | DZ-12 (ng/ml) | ML-13 (ng/ml) | LM-14 (ng/ml) | ST-15 (ng/ml) | IJ-16 (ng/ml) | Mean | Std. Dev. | SEM | CV |
|---|---|---|---|---|---|---|---|---|---|---|
| 1 | 0.000 | 0.000 | 0.000 | 0.000 | 0.000 | 0.000 | 0.000 | 0.000 | 0.000 | 0.000 |
| 2 | 0.193 | 0.134 | 0.240 | 0.182 | 0.175 | 0.217 | 0.180 | 0.076 | 0.019 | 0.421 |
| 3 | 0.171 | 0.174 | 0.189 | 0.229 | 0.181 | 0.239 | 0.221 | 0.047 | 0.012 | 0.212 |
| 4 | 0.146 | 0.197 | 0.204 | 0.268 | 0.230 | 0.295 | 0.232 | 0.047 | 0.012 | 0.201 |
| 5 | 0.100 | 0.214 | 0.168 | 0.254 | 0.199 | 0.246 | 0.212 | 0.054 | 0.014 | 0.257 |
| 6 | 0.198 | 0.196 | 0.145 | 0.185 | 0.202 | 0.228 | 0.203 | 0.045 | 0.011 | 0.222 |
| 7 | 0.202 | 0.224 | 0.162 | 0.189 | 0.192 | 0.179 | 0.190 | 0.059 | 0.015 | 0.310 |
| 8 | 0.176 | 0.216 | 0.201 | 0.177 | 0.185 | 0.141 | 0.198 | 0.056 | 0.014 | 0.285 |
| 9 | 0.156 | 0.185 | 0.240 | 0.174 | 0.154 | 0.138 | 0.164 | 0.039 | 0.010 | 0.239 |
| 10 | 0.154 | 0.185 | 0.155 | 0.151 | 0.159 | 0.127 | 0.142 | 0.039 | 0.010 | 0.276 |
| 11 | 0.151 | 0.113 | 0.152 | 0.142 | 0.088 | 0.122 | 0.148 | 0.049 | 0.012 | 0.330 |
| 12 | 0.164 | 0.106 | 0.115 | 0.134 | 0.078 | 0.119 | 0.134 | 0.055 | 0.014 | 0.415 |
| 13 | 0.132 | 0.097 | 0.097 | 0.052 | 0.065 | 0.085 | 0.119 | 0.067 | 0.017 | 0.567 |
| 14 | 0.082 | 0.080 | 0.092 | 0.018 | 0.056 | 0.067 | 0.092 | 0.058 | 0.014 | 0.628 |
| 15 | 0.026 | 0.073 | 0.052 | 0.070 | 0.023 | 0.042 | 0.059 | 0.028 | 0.007 | 0.473 |
| 16 | 0.014 | 0.015 | 0.071 | 0.004 | 0.012 | 0.014 | 0.026 | 0.020 | 0.005 | 0.759 |

Whereas particular embodiments of this invention have been described above for purposes of illustration, it will be evident to those skilled in the art that numerous variations of the details of the present invention may be made without departing from the invention as defined in the appended claims.

What is claimed is:

1. A method of administering a pharmaceutical agent to the buccal mucosae of a patient comprising:

spraying a composition comprising said pharmaceutical agent in micellar form to said buccal mucosae with a metered dose dispenser, wherein said pharmaceutical agent is selected from the group consisting of insulin, heparin, low molecular weight heparin, hirulog, hirugen, huridine, interferons, cytokines, mono and polyclonal antibodies, immunoglobins, chemotherapeutic agents, vaccines, glycoproteins, bacterial toxoids, hormones, calcitonins, glucagons like peptides, antibiotics, thrombolytic compounds, platelet inhibitors, DNA, RNA, gene therapeutics, antisense oligonucleotides, hypnotics, steroids, opioids, and painkillers, and wherein said pharmaceutical agent is absorbed through said buccal mucosae and a peak plasma level of said pharmaceutical agent is obtained in less than about 1 hour.

2. The method of claim 1, wherein said composition further comprises at least three micelle-forming compounds, said pharmaceutical agent is absorbed through the buccal mucosae, and a peak plasma level of said pharmaceutical agent is obtained in less than about 45 minutes.

3. The method of claim 2, wherein a peak plasma level of said pharmaceutical agent is obtained in less than about 30 minutes.

4. The method of claim 1, wherein said pharmaceutical agent is insulin.

5. The method of claim 3, wherein said pharmaceutical agent is insulin.

6. A method of enhancing absorption of a pharmaceutical agent administered to the buccal mucosae of a patient comprising:

spraying a composition comprising said pharmaceutical agent in micellar form to said buccal mucosae with a metered dose dispenser, wherein said pharmaceutical agent is selected from the group consisting of insulin, heparin, low molecular weight heparin, hirulog, hirugen, huridine, interferons, cytokines, mono and polyclonal antibodies, immunoglobulins, chemotherapeutic agents, vaccines, glycoproteins, bacterial toxoids, hormones, calcitonins, glucagons like peptides, antibiotics, thrombolytic compounds platelet inhibitors, DNA, RNA, gene therapeutics, antisense oligonucleotides, hypnotics, steroids, opioids fentanyl and pain killers, and wherein said pharmaceutical agent is absorbed through said buccal mucosae and a peak plasma level of said pharmaceutical agent is obtained in less than about 1 hour.

7. The method of claim 6, wherein said composition further comprises at least three micelle-forming compounds, said pharmaceutical agent is absorbed through the buccal mucosae, and a peak plasma level of said pharmaceutical agent is obtained in less than about 45 minutes.

8. The method of claim 7, wherein a peak plasma level of said pharmaceutical agent is obtained in less than about 30 minutes.

9. The method of claim 6, wherein said pulmonary pharmaceutical agent is insulin.

10. The method of claim 8, wherein said pulmonary pharmaceutical agent is insulin.

11. The method of claim 6, wherein said pharmaceutical agent is fentanyl.

12. The method of claim 8, wherein said pharmaceutical agent is fentanyl.

13. A method of administering a pharmaceutical agent to the buccal mucosae of a patient comprising:

spraying a composition comprising said pharmaceutical agent and at least three micelle-forming compounds in micellar form to said buccal mucosae with a metered dose dispenser, wherein said pharmaceutical agent is selected from the group consisting of insulin, heparin, low molecular weight heparin, hirulog, hirugen, huridine, interferons, cytokines, mono and polyclonal antibodies, immunoglobins, chemotherapeutic agents, vaccines, glycoproteins, bacterial toxoids, hormones, calcitonins, glucagons like peptides, antibiotics, thrombolytic compounds, platelet inhibitors, DNA, RNA, gene therapeutics, antisense oligonucleotides, hypnotics, steroids, opioids, and pain killers, and wherein said pharmaceutical agent is absorbed through said buccal mucosae and a peak plasma level of said pharmaceutical agent is obtained in less than about 1 hour.

14. The method of claim 13, wherein a peak plasma level of said pharmaceutical agent is obtained in less than about 30 minutes.

15. A method of administering insulin to the buccal mucosae of a patient comprising spraying a composition comprising said insulin and at least three micelle-forming compounds in micellar form to said buccal mucosae with a metered dose dispenser, wherein said insulin is absorbed through said buccal mucosae and a peak plasma level of said insulin is obtained in less than about 1 hour.

16. The method of claim 15, wherein a peak plasma level of said insulin is obtained in less than about 30 minutes.

* * * * *